United States Patent [19]
Heiber et al.

[11] Patent Number: 4,911,707
[45] Date of Patent: Mar. 27, 1990

[54] MONOLITHIC USER-ACTIVATED TRANSDERMAL THERAPEUTIC SYSTEM

[75] Inventors: Werner Heiber, Bedford Hills; Robert Andriola, Putnam Valley, both of N.Y.; Paul Williams, Fairlawn, N.J.; Charles Ebert, Redwood City, Calif.

[73] Assignee: Ciba-Geigy Corporation, Ardsley, N.Y.

[21] Appl. No.: 231,633

[22] Filed: Aug. 10, 1988

Related U.S. Application Data

[63] Continuation of Ser. No. 14,313, Feb. 13, 1987, abandoned.

[51] Int. Cl.$^4$ .............................................. A61F 13/00
[52] U.S. Cl. .................................... 424/449; 604/306; 604/307; 424/448
[58] Field of Search ............... 604/416, 304–308, 604/896.1, 897.1, 890.1, 892.1; 128/156; 206/219, 221; 424/447–449

[56] References Cited

U.S. PATENT DOCUMENTS

| 3,053,255 | 9/1962 | Meyer | 604/307 |
|---|---|---|---|
| 3,306,292 | 2/1967 | Spees | 128/156 |
| 3,565,075 | 2/1971 | Jerry | 128/156 |
| 3,580,254 | 5/1971 | Stuart | 128/156 |
| 3,702,677 | 11/1972 | Heffington | 239/55 |
| 3,797,492 | 3/1974 | Place | 604/890.1 |
| 3,797,494 | 3/1974 | Zaffaroni | 424/434 |
| 4,320,759 | 3/1982 | Theeuwes | 604/892.1 |
| 4,449,983 | 5/1984 | Cortese et al. | 604/892.1 |
| 4,476,976 | 10/1984 | Smith | 206/219 |
| 4,526,176 | 7/1987 | Bremer et al. | 128/156 |
| 4,597,961 | 7/1986 | Etscorn | 424/448 |
| 4,608,043 | 8/1986 | Larkin | 604/87 |
| 4,635,624 | 1/1987 | Gilman | 128/156 |
| 4,645,502 | 2/1987 | Gale et al. | 604/896.1 |
| 4,666,441 | 5/1987 | Andriola et al. | 604/303 |
| 4,687,476 | 8/1987 | Pailin | 128/156 |
| 4,693,706 | 9/1987 | Ennis, III | 604/56 |
| 4,693,711 | 9/1987 | Bremer et al. | 604/306 |
| 4,781,924 | 11/1988 | Lee et al. | 424/449 |

FOREIGN PATENT DOCUMENTS 252459  1/1988  European Pat. Off. .
0992459 5/1965  United Kingdom ................ 206/219

OTHER PUBLICATIONS

Abstract of German 3439239A (1986).

Primary Examiner—C. Fred Rosenbaum
Assistant Examiner—Sharon Rose
Attorney, Agent, or Firm—Irving M. Fishman

[57] ABSTRACT

A transdermal drug delivery system which is manufactured in a pre-activated state for at least one of storage stability, manufacture safety, user safety, or control of release characteristic considerations and which is activated by a patient (or other person applying the system to the patient) just prior to or immediately after applying the system to the patient's skin is disclosed.

20 Claims, 1 Drawing Sheet

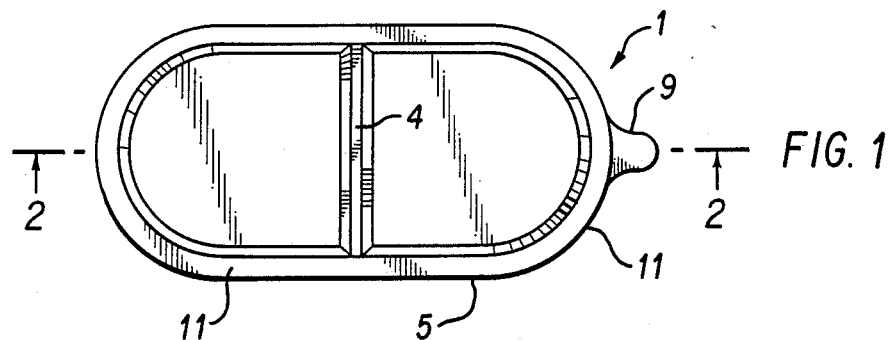
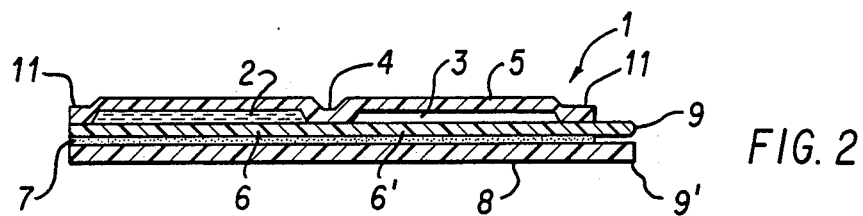
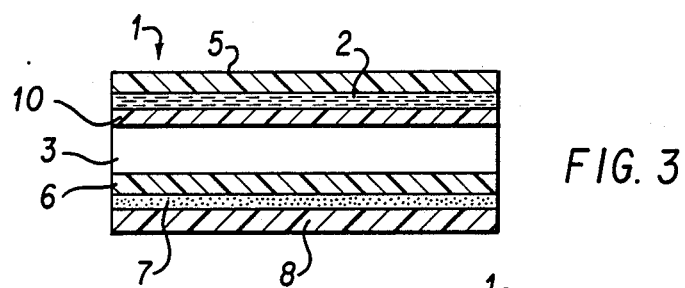
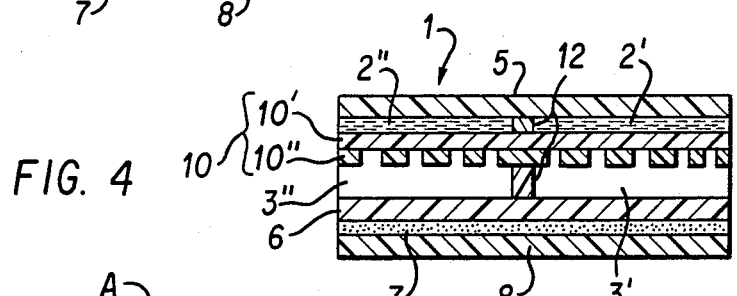
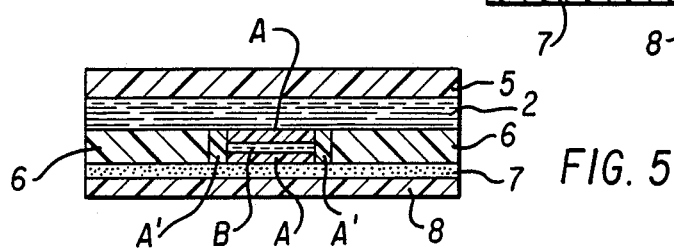

MONOLITHIC USER-ACTIVATED TRANSDERMAL THERAPEUTIC SYSTEM

This application is a continuation of application Ser. No. 014,313, filed Feb. 13, 1987, now abandoned.

FIELD OF THE INVENTION

The instant invention relates to improved transdermal drug delivery systems. In the systems of the invention, the active agent is in a form which (a) does not migrate beyond the limits of its monolithic reservoir, and/or (b) is less active, less toxic, and/or more stable than the form of the active agent which would otherwise be administered by the transdermal route until such time as the system is activated by the user. Activation is achieved by contacting an activating substance with the active agent monolithic reservoir and/or the active agent reservoir contents, which activating substance has been physically separated from the agent to be activated and active agent reservoir.

BACKGROUND OF THE INVENTION

Transdermal drug delivery systems have, in recent years, become an increasingly important means of administering drugs. Such systems offer advantages which are clearly not achievable by other modes of administration such as avoidance of the gastro-intestinal tract and "first-pass" through the liver, application close to the site of action, sustained action which can readily be adjusted, etc. Clearly then, such systems will become of even greater significance in the future.

Typical transdermal systems currently known are disclosed in U.S. Pat. Nos. 3,598,122; 3,598,123; 3,742,951; 3,797,494; 3,948,254; 3,996,934; 4,284,444; and 4,597,961. These systems fall essentially into two catagories, the "matrix" resevoir type and the "membrane bag" reservoir type. Each type has some kind of backing material, a drug reservoir, and an adhesive. The backing material is inert to the drug (or drug formulation) and adhesive and does not permit any of the drug formulation to migrate through it.

In matrix type systems, the drug resevoir is a matrix in which the drug is dispersed and through which it may migrate by diffusion or microporous flow. The matrix material may simultaneously act as an adhesive as well; in which case only an occlusive, removeable covering is required to complete the system. When the matrix material is not an adhesive, a suitable adhesive is also necessary to mount the matrix on the backing material as well as to the removeable occlusive covering. Alternatives to adhesives to secure the "matrix" to the backing material and removeable occlusive covering include compression fitting and "hot melting" including thermal impulse and ultrasonic welding.

In "membrane bag" type systems, a drug permeable membrane is mounted on the backing layer to define a pouch (either by adhesive, compression fitting or hot melting) or two membranes are sealed together to define a "bag" which is mounted on the backing with a suitable adhesive. Adhesive is also required on the bag's surface distal to the backing layer to affix an occlusive removeable covering.

In each of these systems the drug contained in the system is, at all relevant times, capable of crossing all of the system components which would be interposed between the drug and the removeable, occlusive covering, or patients skin.

While these known systems are quite useful, they also have severe drawbacks and limitations to their use. One of the most important drawbacks of the known transdermal systems is intimately related to the properties which make the route of administration possible at all, the ability to permeate intact skin. Because the active agent can (or the formulation containing it permits it to) permeate intact skin and quite potent agents are being used, extreme caution must be used in the manufacturing process. Here, bulk quantitites of potent agents are being utilized and even minor "accidents" can result in severe medical emergencies. Small amounts which contaminate clothes can find their way onto worker's skin and then into their bodies. As such workers deal with the drug on a frequent basis, unless the utmost care is taken, these people can receive many times the therapeutic dose of the active agent. This problem is of even greater concern when the active agent has a high vapor pressure resulting in vapor settling on clothes, uncovered skin, or elsewhere.

Another problem of the known transdermal systems is that frequently the permeating form of the drug is not suitably stable; therefore, the shelf life of the system would be too short to be commercially practical. A third problem encountered by the known transdermal systems is the problem of "drug leakage", primarily through the adhesive. The drug must be able to migrate through or around the adhesive. Since it can, it will redistribute itself from the reservoir into the adhesive, and if the adhesive (and permeable membrane) have edges which are not surrounded by an occlusive covering, drug loss results.

In addition, transdermal systems of the art are limited to regulating drug delivery by only a few, very limited means; drug concentration, membrane or matrix material and thickness, and flux enhancers. However, once the parameters are chosen, only a single release rate results per system. The only exception to this is in the case where the adhesive between the reservoir and the removeable, occlusive covering absorbs a portion of the drug. In this case, an initial "burst" effect is observed. The amount of drug initially delivered is higher and then tapers off to a sustained release level.

Another problem encountered with known transdermal devices is how to know when it is time to change the device for a fresh one. Dosing of any medication, by almost any route of administration, has largely been one of "approximately" and "trial and error". This is especially so with respect to ambulatory patients and long term medication.

Therefore, one of the objects of the invention is to provide a transdermal system which overcomes these and other defects.

It is an object of the invention to provide a transdermal system which can be manufactured with greater safety with a broader range of active agents than previously possible.

It is another object of this invention to provide a transdermal system which is less hazardous to the user during its application to the patients skin.

It is an additional object of the invention to provide a transdermal system which has greater storage stability than the known systems.

Another object of the invention is to provide a transdermal system whose release characteristics can be designed in a manner to allow a complex arrangement of drug delivery regimens in a single system.

A still further object of the invention is to provide a change in the device perceptible to the user to indicate the system no longer contains an adequate drug supply.

A still further object is to deliver topical drugs to a patient's skin in accordance with the foregoing objects.

SUMMARY OF THE INVENTION

These and other objects are achieved by the instant invention which is an improved monolithic transdermal system having at least two physically distinct reservoirs. In one reservoir is an activating substance. The second reservoir corresponds to the prior art monolithic reservoirs mentioned above. The barrier separating the reservoirs does not allow passage of the activating substance. That barrier is breached by action of the user just prior to or shortly after application of the system, whereby the activating substance activates the system. Upon activation of the system, the drug can migrate to and through the skin and carry out its function.

BRIEF DESCRIPTION OF THE DRAWINGS

FIG. 1 is a top view of one embodiment of the invention having the reservoir areas side by side and a monolithic layer (not visible) therebelow.

FIG. 2 is a cross-section view of FIG. 1 along line 2—2.

FIG. 3 is a cross-section of another embodiment of the invention having the reservoirs stacked, rather than side by side.

FIG. 4 is a cross-section of still another embodiment of the invention having more than the reservoirs shown in the other Figures.

FIG. 5 is a cross-section of an embodiment of a membrane activation system according to the invention.

DETAILED DESCRIPTION OF THE DRAWINGS

FIGS. 1 and 2 represent a first embodiment of the invention. As shown, the bottom most layer 8 is a removeable protective layer which is taken off transdermal patch 1 by a user or other person just prior to applying the remainder of the patch to a patient's skin. The remainder of the patch, comprising components 2–7, 9, and 11, is applied to the patient as a unit, with the monolithic active agent precursor containing layer 7 contacting the skin. Layer 7 is also in contact with permeable membrane 6', and if present, impermeable membrane 6. If the monolithic matrix has adhesive as apart thereof, no additional adhesive is needed. If not, a thin layer of adhesive sufficient to adhere the monolithic layer to the rest of the system (and the patient) is also required on the appropriate surfaces. This "coating", if present, is not separately shown in the figures, but considered to be the edging of layer 7 as shown. Impermeable backing membrane 5 is sealed to permeable membrane 6' and impermeable membrane 6, and together membranes 5, 6 and 6' define two reservoir areas 2 and 3 therebetween. The two reservoir areas are separated by a pressure sensitive seal 4.

Reservoir area 2 contains an activating substance while area 3 is empty. The agent to be activated is distributed in monolithic layer 7, either throughout the entire area or only in that region covering area 3. Alternatively, membranes 6 and 6' may be of the same material provided it is impermeable to two substances, which substances, when mixed, generate an activating substance which can permeate membrane 6—6'. In that event, one of the activating substance precursors are contained in area 2 and the other in area 3.

First tab 9' is a portion of the protective layer 8 which is not coated with adhesive and juts out from the rest of patch 1 so as to facilitate removal of protective layer 8. Second tab 9 is also not coated with adhesive and is used to remove the patch from the patient's skin. It is irrelevant which portion, around the perimeter of the patch, as viewed in FIG. 1 has tabs 9 and 9'. Tab 9 can be an extension of either membrane 6 or 6'.

As viewed from the top (see FIG. 1), the patch overall perimeter (exclusive of the tab) can be of any desirable configuration. However, that shown in FIG. 1 and circular are preferable.

This embodiment is typically prepared as follows: A silanized polyester (or other suitable material treated with a releasing agent), approximately 75 micron thick, is used as removable layer 8. Onto this is cast a monolithic layer containing contact adhesive, layer 7, typically a polyisobutylene containing solution. This is further laminated to a membranes 6—6', if desired, about 100 microns thick. Ethylene-vinyl acetate is quite suitable for this membrane but others known in the art will be apparent. Next, the contents of reservoir 2 (and 3 if any) is dispensed, in a suitable form, on membranes 6—6', and a suitable backing layer (about 80 micron) having a heat sealable coating on one surface is placed over the reservoir contents, coated side against the contents, and the device is heat sealed around the perimeter, seal 11, and between the two reservoirs, heat seal 4.

The dimensions of heat seal 4 (preferably about 0.5 to about 2.0, more preferably about 0.5 to about 1.0 mm wide) and the seal(s) around the perimeter of the patch are such that seal 4 will selectively burst under pressure applied by the "user", advantageously at about 10 pounds of force to about 50 pounds of force. The minimum force to burst a burstable seal may be as high as about 20 pounds, preferably 17, more preferably 14, most preferably 10 pounds of applied force.

Throughout this specification, and claims the term "applied force", unless otherwise characterized, means the total force ultimately translated to the burstable portions of the system.

As a practical matter, the burstable seal must be capable of bursting under pressures which will be commonly applied by those using or applying the system. Hence, a system having burstable seals which burst only upon an applied force in excess of 50 pounds is generally not suitable. However, seals which burst only at applied forces greater than 50 pounds, if desired, could certainly be used even though such systems might have limited patient acceptability. Preferably, the maximum applied force required to burst the burstable seal is about 40 pounds, more preferably 30 pounds, most preferably 20 pounds. The only real limitation within these bounds is that the non-burstable seals and membranes be capable of maintaining their integrity at the applied forces. Hence, such non-burstable seals and membranes must be of sufficient size and material to remain intact under a pressure in the range of at least 20 pounds up to 60 pounds applied force. Preferably, the non-burstable portions of the system are of such size and materials so that they can withstand a force preferably at least 1.5, more preferably at least 2.0, most preferably 2.5, times that required to burst the burstable seal.

A second embodiment is shown in FIG. 3 (seal 11 and tabs 9 and 9' not being shown) wherein the reservoir areas 2 and 3 are on top of another and separated by pressure sensitive, non-permeable membrane 10. The pressure sensitive, non-permeable membrane 10 shown in this embodiment is a single layer of continuous material; however it may be depth slit or a laminate of a continuous sheet and perforated sheet of membrane material. The limitations in the preceeding paragraph regarding applied force are applicable here as well, pressure sensitive membrane 10 replacing burstable seal 4 in the description there.

Advantageously, in the laminate, the continuous material is about 10 to about 50 microns and the perforated material independently about 10 to about 100 microns thick. More specifically, the continuous material is suitably 50, preferably 41, more preferably 33, and most preferably 25 microns thick; while the perforated material is suitably 100, preferably about 83, more preferably 66 and most preferably 50 microns thick. Alternatively, a continuous sheet of material can be 'depth slit' to a suitable degree. These dimensions are given when the laminate membrane materials are ethylene/vinyl acetate copolymer. Use of different laminate materials having different strengths will lead to slightly different relative dimensions of thickness of the continuous and perforated materials. However, it should be realized that any degree of selectively re-inforcing only portions of the burstable membrane aid in the performance of the system.

The above laminate, when used, is placed over the contents of reservoir 3 (if any), with the weakened surface of the laminate preferably facing reservoir 3, the contents of reservoir 2 and backing layer 5 applied, and the entire assembly sealed. In this system, reservoir area 3 is empty and reservoir 2 contains an activating substance or reservoir 2 and 3 contain substances that, when mixed, generate an activating substance. In such an embodiment having substances in both areas 2 and 3, membrane 10 must be impermeable to both, while membrane 6 should be impermeable to the substance in reservoir 3 if it is capable of activating the active agent precursor, but otherwise, membrane 6 need not be impermeable.

In any embodiment where reservoir 2 contains an activating agent (not a precursor) and membrane 10 is a laminate of a continuous sheet of impermeable membrane and a perforated sheet of a membrane, reservoir 3 (other than the perforation space), reservoir 3's contents, and membrane 6 can be eliminated. In other words, the perforated side of laminate layer 10 is in direct contact with monolithic solid matrix layer 7.

Suitable alternative materials and dimensions for layers 5-9 are known in the transdermal art as apparent from the aforementioned U.S. patents.

Layer 10 can be selected from any suitable membrane material which is known which can maintain a separation between the contents of reservoir 2 and reservoir 3 (when present) or between reservoir 2 and layer 7. Most preferably, layer 10 is a polyolefin (for example ethylene/vinyl acetate or polyethylene).

In any event, when membrane 10 is present, the burstable portion of the membrane (i.e. non reinforced areas thereof) is no greater than about 20% to 80%, preferably about 20% to about 50%, as thick as any other membrane made of the same material in the system.

As one of ordinary skill will be aware, other embodiments include combinations of features of the foregoing embodiments. One such variation is the embodiment of FIG. 4. This differs from FIG. 3 in that reservoirs 2 and 3 have been split into two compartments each 2', 2'', 3' and 3'', by nonburstable, nonpermeable membranes (or nonburstable seals) 12, and membrane 10 is shown in the laminate form as layers 10' and 10''. Membrane (or seal) 12 must meet the same requirements for nonburstability as set forth earlier for other nonburstable seals or membranes in the system. Such a system can be utilized to administer more than one therapeutic agent at a time when those agents are either chemically incompatable, require incompatable activating substances, cannot come in contact with the activating substance of the other therapeutic agent, or require different flux enhancers. Still other variations of construction and utilities for the more complex systems will be apparent to those of ordinary skill. Of course, as stated above, where desired, empty reservoir areas (such as 3' and 3'') in appropriate circumstances (other than the "perforation space") and membrane 6 can be eliminated if desired.

A further variation of the embodiments described above is the inclusion of a user perceptible timing indicator to alert patients or those administering the patches to patients that the transdermal device has been exhausted, is near exhaustion, or is otherwise depleted to an extent that desired delivery characteristics are no longer being met. The timing device can be a non-permeable ingredient which changes color over time once activation of the system has occurred, a non-permeable colored ingredient which has been encapsulated, with the encapsulating material degrading over time once activation has occurred, or most advantageously, a non-permeable color changing ingredient which color change results from the depletion of the active agent itself.

Generally, the user bursts the barrier (seal 4 or membrane 10) immediately before or after applying the patch to the skin. This now allows the contents of reservoirs 2 and 7 to come into contact, whereby the system is activated. Usually, the therapeutic agent is in a form which must be altered for the desired transdermal delivery, and the activating substance transforms the therapeutic agent into the suitable species. However, it is not critical that the therapeutic agent be altered. It is only required that until the barrier between the reservoir and the monolithic matrix is breached, the system as a whole be in the inactive state. As such, systems wherein the activating substance alters the permeability characteristics of the layers between reservoir 2 and the skin so that the unchanged therapeutic agent can then migrate to and through the skin are also within the scope of the invention.

As noted above, the critical feature of the invention is that until the activating substance is brought into contact with the inactive form of the therapeutic agent and/or the barrier between the therapeutic agent and the removeable occlusive layer or skin, the system is essentially inactive. Once this contact has been made, the system is activated and drug flow from the reservoir to the skin begins.

When a heat seal is used as the barrier between the reservoirs, heat seal 4 should be significantly thinner than the perimeter seals so that seal 4 is preferentially burst when placed under pressure. In order to insure that heat seal 4 doesn't inadvertantly burst under normal handling, it should be of sufficient thickness to resist a pressure of up to about 5 to up to about 15 pounds applied force, preferably about 10 to about 15 pounds, more preferably 10 pounds of applied force. Advantageously, upon the application of forces in excess of about 5 to about 20, preferably about 10 to about 15, more preferably about 10, seal 4 will burst. However, seal 4 may resist greater forces, as set forth earlier, if desired.

When a membrane barrier is used, such as membrane 10, it can be constructed of the same or different materials as the other membranes of the system. If membrane 10 is of the same material as the other membranes, the unreinforced area should be significantly thinner than other membranes to insure selective bursting of barrier membrane 10. If desired, the reinforcing portion of barrier membrane 10 may be omitted, but it is most preferably present. If a different membrane material is selected for the unreinforced portion of barrier membrane 10, it can be of any appropriate thickness which will preferentially burst vis-a-vis the other membranes and seals when subjected to the applied forces in the range of 10 to 50 pounds as set out above. As noted above with respect to seal 4, barrier membrane 10, whether reinforced or not, must be resilient enough to resist bursting unintentionally under normal handling conditions.

There are a variety of "inactive" forms of the therapeutic agent and corresponding activating substance suitable for the instant invention. These include the therapeutic agent being a powder, a crystal, in an ionized form, being bound to an ion exchange resin or covalently coupled via labile linkages to an immobilizing moiety, being trapped in a polymer matrix, being encapsulated with an appropriate material, being in the form of a precursor or prodrug, or combinations thereof. Many other forms will be apparent to those of ordinary skill and are within the scope of the invention.

Preferably this form of the therapeutic agent will not traverse the skin and/or at least one barrier of the system between the therapeutic agent and the skin (or removeable, protective layer 8). However, in the event one merely wishes to reduce the "hazards of manufacture and storage" these therapeutic agent forms may still be able to penetrate from the system into the skin before activation, but the activated form is the desired form to be administered. This may be exemplified by an application of an acidic drug, where the ionized species penetrates to a slight degree, but the free acid permeates through the appropriate barrier to a much larger degree and freely permeates through the skin. Upon application, but before activation, only a very low dose would be delivered. Upon activation, the much larger desired dose would reach the patient.

The activating substances are any appropriate substances which change the therapeutic agent form into one which will deliver the desired dose at the desired rate to the patient. These include solvents such as water, alcohol, etc; pH regulators such as buffers, acids, or bases; salt solutions to elute the drug; enzymes or catalysts to cleave labile linkages; swelling agents to open microencapsulation pores; appropriate reactive species to generate the drug from the prodrug or precursor; etc.

In other embodiments, the barrier between the activating substance and the monolithic layer is altered so as to achieve activation. Such a system is exemplified by FIG. 5. In this Figure, permeable membrane 6 might be a xerogel or ionic gel which is not permeable to the activating substance or formulation thereof until it is hydrated. Compartment B would contain water or buffer in a water impermeable casing of membrane A and A'. Depending upon the desired characteristics, activation could be achieved by selectively breaking the sidewalls of compartment B (walls A') and hydrating xerogel or increasing hydration of the ionic gel membrane 6. Once hydrated, the pores in membrane 6 will allow the passage of the activating substance in reservoir 2. A typical example is a crosslinked polyacrylic acid membrane 6 and a basic agent. When walls A' are broken, the polyacrylic acid pores open under the action of the basic agent so that the drug to be administered can migrate through the system.

In each embodiment described above, the activating agent can, instead of altering drug from or solubilizing the drug found in the monolithic layer, alter the characteristics of the monolithic layer itself. For example, a drug which itself is unaffected by the activating agent can be immobilized within the monolithic layer due to pore size. So long as the pore size is small, the drug cannot migrate, but otherwise, migration and skin permeation would be possible. Upon contact of the activating substance with the monolithic layer matrix, the matrix swells, expanding pores, and allows the drug to migrate.

While virtually any drug can be administered transdermally (see for example U.S. Pat. Nos. 3,598,122; 3,598,123; 3,742,951; 3,797,494; 3,948,254; 3,996,934; 4,284,444; and 4,597,961; etc.) with the present system, it is especially useful to use the present invention to administer a drug selected from: antitubercular agents, such as isoniazid and rifampin; analgesics such as fentanyl and sufentanyl; muscle relaxants, such as baclofen; $\beta$-adrenergic receptor agonists and antiasthmatics, such as theophylline, formoterol, and terbutaline; steroids, such as estradiol, progesterone, methyltestosterone, and desoxycorticosterone, anticholinergics, such as scopolamine and methscopolamine; vasodilators, such as nitroglycerine; antihypertensives, such as metoprolol; antihistamines, such as triprolidine, tripelenamine, and diphenhydramine; cholinergic agents, such as arecoline; CNS stimulants, such as methylphenidate and nikethimide; angiotensin converting enzyme inhibitors, such as 3-[(5-amino-1-carboxy)pentyl-amino]-1-carboxymethyl-2,3,4,5-tetrahydro-1H-1-benzazepine-2-one; nicotine, physostigmine, and naloxone. The only limitation to use of this system for a drug for transdermal use is that the drug have at least one form which permeates through the skin and any barriers of the system between the drug reservoir and the skin. If a topical drug is being administered, the only restriction is that there be at least one form of the drug which can migrate through the system barriers between the drug reservoir and the skin. Of course, any of the drugs which are known in the art to be transdermally administrable can be administered with the present system.

A preferred class of drugs for use in the system of the invention is: fentanyl, sufentanyl, terbutaline, formoterol, theophylline, estradiol, progesterone, scopolamine, nitroglycerine, triprolidine, tripelenamine, diphenhydramine, arecoline, nicotine, and 3-[(5-amino-1-carboxy)pentyl-amino]-1-carboxymethyl-2,3,4,5-tetrahydro-1H-1-benzazepine-2-one. A still more preferred group of drugs for use in the invention includes: arecoline, nicotine, progesterone, triprolidine, diphenhydramine, formoterol, scopolamine, nitroglycerine and estradiol. A most preferred drug for administration with the invention is selected from arecoline, nicotine, scopolamine, nitroglycerine and estradiol.

The invention will be further understood in connection with the following Examples which do not limit, but only exemplify, the invention.

EXAMPLE 1

A transdermal drug delivery system according to the invention, essentially as in FIG. 3 (membrane 6 and reservoir 3 are eliminated), is prepared as follows:

A solid matrix monolithic drug reservoir is prepared by extruding poly-ethylene vinyl acetate (EVA) mixed with Arecoline Hydrobromide as an about 200 micron thick film, thus forming a porous monolithic matrix containing 50 to 60% drug by weight. Drug/polymer discs, corresponding to desired system surface areas, are then punched from the extruded film. A pressure sensitive membrane (10 in FIG. 3) is prepared by laminating a previously perforated EVA film (about 50 microns thick) with a continuous EVA film (about 10 microns thick) to form a net membrane laminate (60 microns thick) consisting of a structurally reinforced film with nonreinforced areas corresponding to the degree of perforation in the laminated film. As mechanical pressure is applied across the membrane, the non-reinforced perfortion selectively ruptures. (An alternate technique to prepare a weakened seam in a membrane is to depth slit an EVA membrane (about 70 microns thick) to produce structurally weakened points about 60 microns deep within the film. As pressure is applied across the film the controlled depth slit regions will selectively rupture.) An activator ointment (at area "2" in FIG. 3) comprising 121.3 mg of $K_2CO_3$ ointment consisting of 51.88% $K_2CO_3$, 1.57% carbopol 934P (a gelling agent) and 46.58% water, is dispensed onto the surface of the pressure sensitive membrane ("10" in FIG. 3) and a non-destructive seal is made between the pressure sensitive membrane and a backing film ("5" in FIG. 3) of polyester having an EVA heat sealable coating. The solid matrix drug/polymers disc is then coated with adhesive (disc plus adhesive is represented by "7" in FIG. 3) and positioned on the perforated or depth slit surface of membrane 10. Finally a 75 micron thick film of sylanized polyester ("8" in FIG. 3) is placed over the exposed adhesive surface of the solid matric drug/polyester disc. The system is activated by applying pressure to the top of backing film "5", thus rupturing pressure sensitive membrane "10". The activator ointment is then drawn into the solid drug/polymer matrix by capillary tension and osmotic pressure, thereby converting impermeable Arcoline HBr to permeable Arecoline free base.

We claim:

1. A monolithic therapeutic substance non-releasing drug delivery system having a removable protective layer thereon, said system comprising
   (a) a monolithic therapeutic substance reservoir containing a therapeutic agent or precursor of said therapeutic agent in a first form which cannot permeate from said therapeutic reservoir through said system to the surface of said system which is or was in contact with said removable protective layer;
   (b) an activating agent reservoir containing a system activating agent;
   (c) a burstable seal or membrane between (a) and (b) which is impermeable to said system activating agent and said therapeutic agent or precursor of said therapeutic agent; and
   (d) an occlusive backing layer; wherein upon bursting of said burstable seal or said burstable membrane, said system activating agent activates said system by contacting and converting said therapeutic agent or precursor of said therapeutic agent from said first form into a therapeutic agent second form which second form migrates from said therapeutic agent or precursor of said therapeutic reservoir to said surface of said system which is or was in contact with said removable protective layer whereby said system becomes a therapeutic substance releasing delivery system.

2. A drug delivery system of claim 1 wherein said burstable membrane and burstable seal are broken by application of a pressure between about 10 and 50 pounds force.

3. A drug delivery system of claim 1 wherein said burstable membrane and burstable seal are a membrane and seal which selectively ruptured as compared to other membranes, seals and layers of said system under pressures of about 10 to about 50 pounds force.

4. A drug delivery system of claim 3 wherein said burstable seal is a heat seal which is no greater than about 1/6 as wide as any other heat seal of the same material in said system.

5. A drug delivery system of claim 3 wherein said burstable heat seal is from about 0.5 to about 2.0 mm wide.

6. A drug delivery system of claim 3 wherein said burstable membrane is selectively reinforced with unreinforced areas being no greater than about 20% to about 80% as wide as any other membrane or layer in said system made of the same material.

7. A drug delivery system of claim 6 where said unreinforced areas of said burstable membrane are no greater than about 10 to about 50 microns thick.

8. A drug delivery system of claim 3 wherein said burstable membrane is a membrane which would otherwise not be burstable under normal use but which has been selectively weakened.

9. A drug delivery system of claim 8 wherein said burstable membrane has been made selectively burstable by controlled depth slitting.

10. A drug delivery system of claim 1 wherein said therapeutic agent is selected from fentanyl, sufentanyl, isoniazid, rifampin, baclofen, terbutaline, theophylline, arecoline, nicotine, progesterone, methyltestosterone, desoxycorticosterone, triprolidine, diphenhydramine, tripelenamine, scopolamine, methscopolamine, nitroglycerine, metoprolol, estradiol, 3-([5-amino-1-carboxyl]-pentylmino)-1-carboxy methyl-2,3,4,5-tetrahydro-1H-1-benzazepine-2-one, formoterol, physostigmine, and naloxone.

11. A monolithic therapeutic substance non-releasing drug delivery system having a removable protective layer thereon, said system comprising
   (a) a monolithic therapeutic substance reservoir containing a therapeutic agent in a form which cannot permeate from said monolithic substance reservoir through said system to the surface of said system which is or was in contact with said removable protective layer;
   (b) an activating agent reservoir containing a system activating agent;
   (c) a burstable membrane or burstable seal between said activating agent reservoir and the portions of said system through which said therapeutic agent must migrate in order to reach said surface which is or was in contact with said removable protective layer but through which said therapeutic agent cannot permeate; and (d) an occlusive backing layer; wherein, upon bursting of said burstable membrane or burstable seal, said activating agent activates said system by contacting said portions through which said therapeutic agent must migrate but cannot migrate to reach the surface of said system which is or was in contact with said removable protection layer and modifying such portions into a form through which said therapeutic agent migrates, whereby said therapeutic agent permeates through said system from said monolithic therapeutic substance reservoir to said surface of said system which is or was in contact with said removable protective layer and said system becomes a therapeutic substance releasing delivery system.

12. A drug delivery system of claim 11 wherein said burstable membrane and burstable seal are broken by application of a pressure between about 10 and 50 pounds force.

13. A drug delivery system of claim 11 wherein said burstable membrane and burstable seal are a membrane and seal which selectively rupture as compared to other membranes, seals and layers of said system, under pressures of about 10 to about 50 pounds force.

14. A drug delivery system of claim 13 wherein said burstable seal is a heat seal which is no greater than about 1/6 as wide as any other heat seal of the same material in said system.

15. A drug delivery system of claim 13 wherein said burstable heat seal is from about 0.5 to about 2.0 mm wide.

16. A drug delivery system of claim 13 wherein said burstable membrane is selectively reinforced with unreinforced areas being no greater than about 20% to about 80% as wide as any other membrane or layer in said system made of the same material.

17. A drug delivery system of claim 16 where said unreinforced areas of said burstable membrane are no greater than about 10 to about 50 microns thick.

18. A drug delivery system of claim 13 wherein said burstable membrane is a membrane which would otherwise not be burstable under normal use but which has been selectively weakened.

19. A drug delivery system of claim 18 wherein said burstable membrane has been made selectively burstable by controlled depth slitting.

20. A drug delivery system of claim 11 wherein said therapeutic agent is selected from fentanyl, sufentanyl, isoniazid, rifampin, baclofen, terbutaline, theophylline, arecoline, nicotine, progesterone, methyltestosterone, desoxycorticosterone, triprolidine, diphenhydramine, tripelenamine, scopolamine, methscopolamine, nitroglycerine, metoprolol, estradiol, 3-([5-amino-1-carboxy]-pentylmino)-1-carboxy methyl-2,3,4,5-tetrahydro-1H-1-benzazepine-2-one, formoterol, physostigmine, and naloxone.

* * * * *